(12) United States Patent
Areskoug et al.

(10) Patent No.: US 6,479,724 B1
(45) Date of Patent: Nov. 12, 2002

(54) WOUND DRESSING

(75) Inventors: Stefan Areskoug, Molnlycke (SE); Bengt W. Lindquist, Lerum (SE)

(73) Assignee: Molnlycke Health Care AB, Gothenburg (SE)

( * ) Notice: Subject to any disclaimer, the term of this patent is extended or adjusted under 35 U.S.C. 154(b) by 0 days.

(21) Appl. No.: 09/701,359
(22) PCT Filed: May 27, 1999
(86) PCT No.: PCT/SE99/00903
   § 371 (c)(1),
   (2), (4) Date: Jan. 18, 2001
(87) PCT Pub. No.: WO99/61077
   PCT Pub. Date: Dec. 2, 1999

(30) Foreign Application Priority Data

May 28, 1998 (SE) ................................................ 9801899

(51) Int. Cl.⁷ ................................................ A61F 13/00
(52) U.S. Cl. .............................. 602/41; 602/42; 602/58; 602/59
(58) Field of Search ............................... 602/41, 42, 44, 602/46, 47, 52, 54, 55, 58, 59

(56) References Cited

U.S. PATENT DOCUMENTS 4,867,150 A  *  9/1989  Gilbert ......................... 602/47
5,635,201 A  *  6/1997  Fabo ............................ 424/443

FOREIGN PATENT DOCUMENTS

| WO | WO 87/05206     | 9/1987  |
| WO | WO 90/14109     | 11/1990 |
| WO | WO 96/09076 A1  | 3/1996  |
| WO | WO 97/42985     | 11/1997 |

* cited by examiner

Primary Examiner—Michael A. Brown
Assistant Examiner—Lalita Hamilton
(74) Attorney, Agent, or Firm—Young & Thompson

(57) ABSTRACT

The present invention relates to a wound dressing that includes a carrier layer which is coated on one side with an adhesive elastomer (3). According to the invention, the carrier layer has the form of a laminate which consists of a plastic film (1) and a material (2) that has an irregular surface structure.

9 Claims, 1 Drawing Sheet

WOUND DRESSING

FIELD OF THE INVENTION

The present invention relates to a wound dressing or an affixing tape for skin applications that includes a carrier layer which is coated on one side with an adhesive elastomer.

BACKGROUND OF THE INVENTION

Thin adhesive wound dressings made from a plastic film that is permeable to water vapor, for instance OpSite® (Smith & Nephew, England) or Tegaderm® (3M, USA), include an acrylate-type adhesive or an adhesive that has similar properties. When repeatedly applied and removed, such adhesives are apt to remove with them parts of the upper skin layer (the stratum corneum) and dressings of this nature can result in skin damage. These adhesives also fasten strongly to hairs on the skin, therewith causing pain and discomfort when removing the dressing.

Also known to the art is a gauze bandage designated Mepitel®, which is affixed to the skin by means of a very soft adhesive silicone elastomer. A silicone elastomer has skin-friendly adhesive properties and is much more gentle to the skin than the aforesaid adhesives. Neither does it tend to strip away parts of the stratum corneum as it is removed. The person wearing such a dressing will not experience discomfort or pain as the dressing is removed. The adhesiveness of the silicone elastomer is not impaired by removal of the dressing, and the dressing can therefore be removed and replaced several times.

Consequently it would be beneficial if the adhesives used with plastic film dressings could be replaced with an adhesive elastomer that has adhesive characteristics similar to those of the silicone elastomers used with Mepitel®, particularly when the dressing is to be placed over sensitive skin. One serious problem in this regard is that such elastomers have been found to adhere to the skin with the same strength as that to which they adhere to the plastic film, and consequently there is a serious risk of the elastomer layer, or large parts thereof, remaining on the skin when attempting to remove the dressing.

SUMMARY OF THE INVENTION

One object of the present invention is to solve this problem and to provide a functional film dressing that includes a layer of soft, adhesive elastomer.

This object is achieved in accordance with the invention by means of a wound dressing or an affixing tape for skin applications which includes a carrier layer that is coated with a soft, adhesive elastomer on one side thereof and which is characterized in that the carrier layer is a laminate that consists of plastic film and a material of irregular surface structure. Because the soft, adhesive elastomer is fastened to the plastic film via the material of irregular surface structure, the elastomer will be anchored more strongly to the film than would otherwise be the case, therewith avoiding the danger of the elastomer remaining on the skin when removing the dressing.

In one preferred embodiment of the invention, the material of irregular surface structure is comprised of nonwoven material, and the soft, adhesive elastomer is comprised of a silicone elastomer.

BRIEF DESCRIPTION OF THE DRAWINGS

The invention will now be described in more detail with reference to the accompanying drawings, in which.

DETAILED DESCRIPTION OF THE INVENTION

Figure 1:
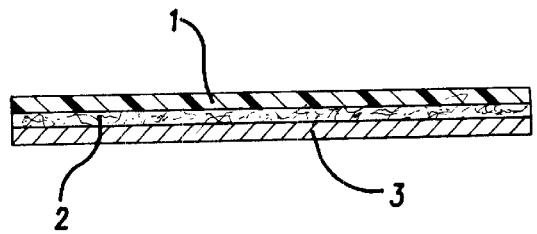
FIG. 1 is a schematic cross-sectional view of one embodiment of an inventive wound dressing.
Figure 2:
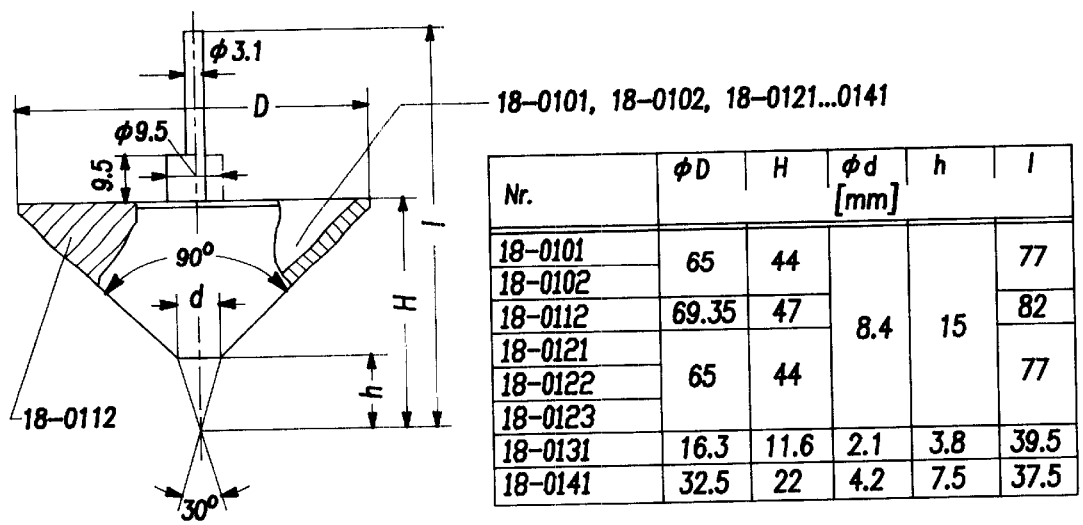
FIG. 2 illustrates a test body for determining softness.

The plastic film wound dressing shown in FIG. 1 includes a layer 1 of plastic film, a thin layer 2 of non-woven material laminated to the plastic film, and a layer 3 of silicone elastomer.

The plastic film is preferably comprised of a polyurethane film that is permeable to water vapor, although other plastic film materials may be used. The non-woven layer has been glued to the plastic film, by heat calandering or in some other appropriate way. The elastomeric layer 3 has been produced by applying a silicone-elastomer mixture to the laminate 1,2 from above with the nonwoven layer facing upwards, said mixture being applied in an amount sufficient to fill completely the fibre structure in said non-woven material and so that surplus elastomer mixture will form a smooth, even surface on top of the laminate. The laminate with its applied layer of elastomer mixture has then been heated until the elastomer mixture has cured to form an elastomer. Because the silicone elastomer extends through all of the free spaces between the fibres in the non-woven material, the elastomer will be anchored effectively in the laminate. Although the illustrated dressing is shown to include three distinct layers, it will be understood from the aforegoing that the silicone elastomer extends through the fibre structure of the layer 2 and up to the plastic film layer 1.

The silicone elastomer is preferably an elastomer retailed under the name Silgel 612 and manufactured by Wacker Chemie GmbH, Germany. Other soft, adhesive silicone elastomers may also be used. Although silicone elastomers are preferred because of the good properties of the silicone in respect of wound care, other soft adhesive elastomers that are skin friendly may also be used, such as hydrogels or soft adhesive hot melt glue.

As beforementioned, the fibre structure of non-woven material provides effective anchoring of the elastomer and is preferred as the anchoring layer. However, other materials that have an irregular surface structure, such as fine-mesh net material, open-structure textile material, thin foam material having open pores, and corresponding materials, can provide sufficiently effective anchoring of the elastomer.

By definition plastic film has a thickness of 5–100 mm, and the anchoring layer will preferably have a weight per unit area of 5–100 g/m2, preferably 15–25 g/m2, so as to ensure that the laminate consisting of the plastic film and the anchoring layer will have the suppleness required.

The wound dressing may, of course, be perforated, especially if it includes an overlaying absorbent pad.

It shall also be possible to sterilise the dressing by means of some conventional sterilisation method, e.g. b-sterilisation, steam sterilisation or sterilisation with ethylene oxide.

The expression "skin-friendly adhesion" is used in this document to characterise a particular form of adhesion exhibited by the soft adhesive elastomers suited for use with the invention.

Different types of self-adhering glues having relatively similar properties are used normally on adhesive dressings and surgical plasters of different kinds. A common feature of the glues normally used is that they adhere to the outermost layer of dead skin cells (stratum corneum) with such firmness that a number of layers of these cells will be stripped from the skin by the glue as the adhesive dressing is removed. The glues used at present are most often acrylate-type glues, although hot melt glues and polyisobuthylene glues are also often used. In the case of skin-friendly glues, the penetration—which constitutes a measurement of softness—shall lie within the range of 7–20 mm, whereas corresponding values for those glues that are normally used with adhesive dressing are less than 3 mm. Penetration is measured by means of a method based on ASTM D 937 and D 51580. Certain modifications are made. The equipment used is a penetrometer PNR 10, Sommer & Runge KG, Germany. A test body weighing 62.5 g and comprising a cone weighing 15 g and bearing article number 18-0122 and a rod weighing 47.5 g and bearing the article number 18-0042 was placed in the penetrometer vertically above a cylindrical cup containing the material to be tested, with the apex of the cone touching the surface of the test material. The test body was then allowed to fall freely down into the cylindrical cup. The extent to which the test body had penetrated the test material was measured after a time lapse of 5 seconds. The cylindrical cup had a diameter of 50 mm and a height of 30 mm. The cup was filled with test material to a level of 25 mm.

The soft elastomers having skin-friendly adhesive properties used in accordance with the present invention had considerably weaker adhesive bonds to the skin than the glues normally used with adhesive dressings. Consequently, elastomers that have skin-friendly adhesive properties leave the stratum corneum essentially intact when dressings containing such elastomers are peeled or pulled away. In spite of the lower adhesive bonds, the elastomers nevertheless create secure and positive adhesion, i.e. there is small risk of the dressing loosening by itself, by virtue of the fact that the softness of the elastomer causes it to flow down into the skin and therewith provide a wide effective contact surface. The softness of the elastomer also results in the build-up of a large amount of energy in the elastomer and its carrier when removing the dressing, which also results in more positive adhesion to the skin.

An experiment was carried out on ten voluntary test persons with the intention of measuring the stripping effect, by which is meant the extent to which the surface of the dressing had become covered with cells as a result of stripping-off the dressing. Four different types of plaster/dressings were used, these being Duoderm®, OpSite®, Leukopore® and an elastomer-coated (200 g/m²) non-woven tape. The soft elastomer having skin-friendly adhesive properties was a silicone type elastomer. Three test samples of each product type were applied to each test person and left in place for 24 hours. The stripping effect was recorded, by coloring the stratum corneum cells present on the surface of the removed dressings selectively with toluidine, whereafter the percentage of the surface covered by cells was determined.

The results are evident from the table below:

| Plaster/dressing | number of dressings with stripping within the range | | |
|---|---|---|---|
| | <1% | –10% | 3 11% |
| Duoderm ® | 0/30 | 0/30 | 30/30 |
| OpSite ® | 0/30 | 0/30 | 30/30 |

-continued

| Plaster/dressing | number of dressings with stripping within the range | | |
|---|---|---|---|
| | <1% | –10% | 3 11% |
| Leukopore ® | 10/30 | 16/30 | 4/30 |
| silicone tape | 27/30 | 3/30 | 0/30 |

In order to be "skin-friendly adhesive", an adhesive dressing shall have a stripping effect of maximum 10% in the case of normal skin.

Because a dressing that includes a skin-friendly adhesive elastomer will only carry with it a very limited number of stratum corneum cells as the dressing is removed, the surface of the elastomer layer will be relatively unchanged after removal of the dressing. This enables a dressing of this nature to be re-applied, since it adhesiveness has not been impaired to any appreciable extent. The adhesive surface of a dressing which pulls stratum corneum cells from the skin will be substantially covered with the cells subsequent to its removal. This means that dressings of this nature will fail to stick to the skin when attempting to re-apply the dressings. Duoderm®, OpSite® and Leukoporev® lose from 70 to 100% of their adhesiveness, whereas skin-friendly adhesive dressings lose less than 10%.

In order for an adhesive dressing or adhesive plaster to function effectively, the force with which it adheres to the skin must exceed the load to which the dressing or plaster is subjected during normal use. It has been found that there is generally required in this respect an adhesive force which exceeds 0,5 N measured when peeling or stripping from the skin a tape measuring 25 mm in width and angled at 135°, so that the danger of the dressing loosening by itself will not be unacceptably high. The adhesive force will preferably exceed 0.8 N/25 mm.

The adhesive force of Duoderm®, OpSite® and Leukopore® was measured at 1.2, 2.2 and 0.8 N/25 mm respectively with tape applied to the backs of healthy test persons and left in place for 24 hours. The silicone tape used in the stripping test above had a skin adhesion strength of 1.5 N/25 mm.

What is claimed is:

1. A wound dressing or an affixing tape for skin applications comprising a carrier layer coated on one side with an adhesive elastomer having adhesive properties with a penetration of 7–20 mm as a measure of softness, wherein the carrier layer is a laminate which comprises a plastic film and a material that has an irregular surface structure having a weight per unit area of 5–100 g/m^2, and wherein the wound dressing has a stripping effect of a maximum of 10% of human skin.

2. The wound dressing according to claim 1, wherein the material of irregular surface structure comprises a non-woven material.

3. The wound dressing according to claim 2, wherein the dressing is perforated.

4. The wound dressing according to claim 3, further comprising an absorbent pad.

5. The wound dressing according to claim 1, wherein the adhesive elastomer comprises a silicone elastomer.

6. The wound dressing according to claim 5, wherein the dressing is perforated.

7. The wound dressing according to claim 6, further comprising an absorbent pad.

8. The wound dressing according to claim 1, wherein the dressing is perforated.

9. The wound dressing according to claim 8, further comprising an absorbent pad.

* * * * *